(12) United States Patent  (10) Patent No.: US 7,909,865 B2
Shanley  (45) Date of Patent: Mar. 22, 2011

(54) EXPANDABLE MEDICAL DEVICE FOR DELIVERY OF BENEFICIAL AGENT

(75) Inventor: John F. Shanley, Redwood City, CA (US)

(73) Assignee: Conor Medsystems, LLC, Menlo Park, CA (US)

( * ) Notice: Subject to any disclaimer, the term of this patent is extended or adjusted under 35 U.S.C. 154(b) by 32 days.

(21) Appl. No.: 12/425,772

(22) Filed: Apr. 17, 2009

(65) Prior Publication Data

US 2009/0276034 A1 Nov. 5, 2009

Related U.S. Application Data

(63) Continuation of application No. 11/368,957, filed on Mar. 6, 2006, which is a continuation of application No. 10/456,292, filed on Jun. 5, 2003, now Pat. No. 7,179,288, which is a continuation of application No. 09/688,092, filed on Oct. 16, 2000, now abandoned, which is a continuation-in-part of application No. 09/183,555, filed on Oct. 29, 1998, now Pat. No. 6,241,762.

(60) Provisional application No. 60/079,881, filed on Mar. 30, 1998.

(51) Int. Cl.
*A61F 2/06* (2006.01)

(52) U.S. Cl. ............... 623/1.42; 623/1.15; 623/1.16; 623/1.44

(58) Field of Classification Search ............ 623/1.42
See application file for complete search history.

(56) References Cited

U.S. PATENT DOCUMENTS

| 3,657,744 A | 4/1972 | Ersek |
| 4,300,244 A | 11/1981 | Bukros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |

(Continued)

FOREIGN PATENT DOCUMENTS

CA 2234787 4/1998

(Continued)

OTHER PUBLICATIONS

Australian Office Action dated May 3, 2010 corresponding to Application No. 2005251777.

(Continued)

*Primary Examiner* — David H Willse
*Assistant Examiner* — Javier G Blanco

(57) ABSTRACT

An expandable medical device having a plurality of elongated struts, the plurality of elongated struts being joined together to form a substantially cylindrical device which is expandable from a cylinder having a first diameter to a cylinder having a second diameter, and the plurality of struts each having a strut width in a circumferential direction. At least one of the plurality of struts includes at least one opening extending at least partially through a thickness of the strut. A beneficial agent may be loaded into the opening within the strut. The expandable medical device may further include a plurality of ductile hinges formed between the elongated struts, the ductile hinges allowing the cylindrical device to be expanded or compressed from the first diameter to the second diameter by deformation of the ductile hinges.

7 Claims, 6 Drawing Sheets

U.S. PATENT DOCUMENTS

| | | |
|---|---|---|
| 4,824,436 A | 4/1989 | Wollinsky |
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Steela et al. |
| 4,969,458 A | 11/1990 | Wiktor |
| 4,989,601 A | 2/1991 | Marchosky et al. |
| 4,990,155 A | 2/1991 | Wilkoff et al. |
| 4,994,071 A | 2/1991 | MacGregor |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya et al. |
| 5,059,211 A | 10/1991 | Stack et al. |
| 5,078,726 A | 1/1992 | Kreamer |
| 5,092,841 A | 3/1992 | Spears |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso |
| 5,439,466 A | 8/1995 | Kilejian |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrx |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,499,373 A | 3/1996 | Richards et al. |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,551,954 A | 9/1996 | Buscemi et al. |
| 5,556,413 A | 9/1996 | Lam |
| 5,578,075 A | 11/1996 | Dayton |
| 5,593,434 A | 1/1997 | Williams |
| 5,595,722 A | 1/1997 | Grainger et al. |
| 5,599,844 A | 2/1997 | Grainger et al. |
| 5,605,696 A | 2/1997 | Eury et al. |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,665,591 A | 9/1997 | Sonenshein et al. |
| 5,667,764 A | 9/1997 | Kopia et al. |
| 5,674,278 A | 10/1997 | Boneau |
| 5,679,400 A | 10/1997 | Tuch |
| 5,697,971 A | 12/1997 | Fischell et al. |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,766,239 A | 6/1998 | Cox |
| 5,769,883 A | 6/1998 | Buscemi et al. |
| 5,770,609 A | 6/1998 | Grainger et al. |
| 5,773,479 A | 6/1998 | Grainger et al. |
| 5,776,181 A | 7/1998 | Lee et al. |
| 5,776,184 A | 7/1998 | Tuch |
| 5,797,898 A | 8/1998 | Santini et al. |
| 5,800,507 A | 9/1998 | Schwartz |
| 5,811,447 A | 9/1998 | Kunz et al. |
| 5,817,152 A | 10/1998 | Birdsall et al. |
| 5,824,045 A | 10/1998 | Alt |
| 5,824,049 A * | 10/1998 | Ragheb et al. ............... 623/1.44 |
| 5,827,322 A | 10/1998 | Williams |
| 5,837,008 A | 11/1998 | Berg et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,928,916 A | 7/1999 | Keogh |
| 5,935,506 A | 8/1999 | Schmitz et al. |
| 5,945,456 A | 8/1999 | Grainger et al. |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz, Jr. et al. |
| 5,992,769 A | 11/1999 | Wise |
| 5,994,341 A | 11/1999 | Hunter et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,056,722 A | 5/2000 | Jayaraman |
| 6,063,101 A | 5/2000 | Jacobsen et al. |
| 6,071,305 A | 6/2000 | Brown et al. |
| 6,074,659 A | 6/2000 | Kunz et al. |
| 6,083,258 A | 7/2000 | Yadav |
| 6,087,479 A | 7/2000 | Stamler et al. |
| 6,120,536 A | 9/2000 | Ding et al. |
| 6,120,847 A | 9/2000 | Yang et al. |
| 6,121,027 A | 9/2000 | Clapper et al. |
| 6,123,861 A | 9/2000 | Santini et al. |
| 6,140,127 A | 10/2000 | Sprague |
| 6,153,252 A | 11/2000 | Hossainy et al. |
| 6,156,062 A | 12/2000 | McGuinness |
| 6,159,488 A | 12/2000 | Nagler et al. |
| 6,171,609 B1 | 1/2001 | Kunz |
| 6,231,600 B1 | 5/2001 | Zhong |
| 6,239,118 B1 | 5/2001 | Schatz et al. |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,268,390 B1 | 7/2001 | Kunz |

| | | |
|---|---|---|
| 6,273,908 B1 | 8/2001 | Ndondo-Lay |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,299,604 B1 | 10/2001 | Ragheb et al. |
| 6,306,166 B1 | 10/2001 | Barry et al. |
| 6,306,421 B1 | 10/2001 | Kunz et al. |
| 6,309,414 B1 | 10/2001 | Rolando et al. |
| 6,312,460 B2 | 11/2001 | Drasler et al. |
| 6,358,556 B1 | 3/2002 | Ding et al. |
| 6,358,989 B1 | 3/2002 | Kunz et al. |
| 6,399,144 B2 | 6/2002 | Dinh et al. |
| 6,403,635 B1 | 6/2002 | Kinsella et al. |
| 6,423,092 B2 | 7/2002 | Datta et al. |
| 6,429,232 B1 | 8/2002 | Kinsella et al. |
| 6,475,237 B2 | 11/2002 | Drasler et al. |
| 6,491,666 B1 | 12/2002 | Santini et al. |
| 6,491,938 B2 | 12/2002 | Kunz et al. |
| 6,497,916 B1 | 12/2002 | Taylor et al. |
| 6,500,859 B2 | 12/2002 | Kinsella et al. |
| 6,503,954 B1 | 1/2003 | Bhat et al. |
| 6,506,411 B2 | 1/2003 | Hunter et al. |
| 6,506,437 B1 | 1/2003 | Harish et al. |
| 6,515,009 B1 | 2/2003 | Kunz et al. |
| 6,537,256 B2 | 3/2003 | Santini et al. |
| 6,544,544 B2 | 4/2003 | Hunter et al. |
| 6,551,838 B2 | 4/2003 | Santini et al. |
| 6,558,733 B1 | 5/2003 | Hossainy et al. |
| 6,562,065 B1 | 5/2003 | Shanley |
| 6,569,441 B2 | 5/2003 | Kunz et al. |
| 6,569,688 B2 | 5/2003 | Sivan et al. |
| 6,599,928 B2 | 7/2003 | Kunz et al. |
| 6,613,084 B2 | 9/2003 | Yang |
| 6,627,246 B2 | 9/2003 | Mehta et al. |
| 6,638,302 B1 | 10/2003 | Curcio et al. |
| 6,645,547 B1 | 11/2003 | Shekalim et al. |
| 6,656,162 B2 * | 12/2003 | Santini et al. ............ 604/191 |
| 6,663,881 B2 | 12/2003 | Kunz et al. |
| 6,673,385 B1 | 1/2004 | Ding et al. |
| 6,682,545 B1 | 1/2004 | Kester |
| 6,702,850 B1 | 3/2004 | Byun et al. |
| 6,712,845 B2 | 3/2004 | Hossainy |
| 6,713,119 B2 | 3/2004 | Hossainy et al. |
| 6,716,442 B2 | 4/2004 | Hunter et al. |
| 6,716,444 B1 | 4/2004 | Castro et al. |
| 6,720,350 B2 | 4/2004 | Kunz et al. |
| 6,723,373 B1 | 4/2004 | Narayanan et al. |
| 6,730,064 B2 | 5/2004 | Ragheb et al. |
| 6,730,116 B1 | 5/2004 | Wolinsky et al. |
| 2001/0018469 A1 | 8/2001 | Chen et al. |
| 2001/0027340 A1 | 10/2001 | Wright et al. |
| 2001/0029351 A1 | 10/2001 | Falotico et al. |
| 2001/0034363 A1 | 10/2001 | Li et al. |
| 2001/0044648 A1 | 11/2001 | Wolinsky |
| 2001/0044652 A1 | 11/2001 | Moore |
| 2002/0002400 A1 | 1/2002 | Drasler et al. |
| 2002/0005206 A1 | 1/2002 | Falotico et al. |
| 2002/0007209 A1 * | 1/2002 | Scheerder et al. ........... 623/1.15 |
| 2002/0007213 A1 | 1/2002 | Falotico et al. |
| 2002/0016625 A1 | 2/2002 | Falotico et al. |
| 2002/0022876 A1 | 2/2002 | Richter et al. |
| 2002/0028243 A1 | 3/2002 | Masters |
| 2002/0032414 A1 | 3/2002 | Ragheb et al. |
| 2002/0038145 A1 | 3/2002 | Jang |
| 2002/0068969 A1 | 6/2002 | Shanley et al. |
| 2002/0071902 A1 | 6/2002 | Ding et al. |
| 2002/0072511 A1 | 6/2002 | New et al. |
| 2002/0082679 A1 | 6/2002 | Sirhan et al. |
| 2002/0082680 A1 | 6/2002 | Shanley et al. |
| 2002/0082682 A1 | 6/2002 | Barclay et al. |
| 2002/0094985 A1 | 7/2002 | Herrmann et al. |
| 2002/0127263 A1 | 9/2002 | Carlyle et al. |
| 2002/0142039 A1 | 10/2002 | Claude |
| 2002/0155212 A1 | 10/2002 | Hossainy |
| 2002/0193475 A1 | 12/2002 | Hossainy et al. |
| 2003/0028244 A1 | 2/2003 | Bates et al. |
| 2003/0036794 A1 | 2/2003 | Ragheb et al. |
| 2003/0050687 A1 | 3/2003 | Schwade et al. |

| | | |
|---|---|---|
| 2003/0060877 A1 | 3/2003 | Falotico et al. |
| 2003/0068355 A1 | 4/2003 | Shanley et al. |
| 2003/0077312 A1 | 4/2003 | Schmulewicz et al. |
| 2003/0083646 A1 | 5/2003 | Sirhan et al. |
| 2003/0086957 A1 | 5/2003 | Hughes et al. |
| 2003/0088307 A1 | 5/2003 | Shulze et al. |
| 2003/0100865 A1 | 5/2003 | Santini et al. |
| 2003/0125803 A1 | 7/2003 | Vallana et al. |
| 2003/0157241 A1 | 8/2003 | Hossainy et al. |
| 2003/0176915 A1 | 9/2003 | Wright et al. |
| 2003/0181973 A1 | 9/2003 | Sahota |
| 2003/0199970 A1 | 10/2003 | Shanley |
| 2003/0204239 A1 | 10/2003 | Carlyle et al. |
| 2003/0216699 A1 | 11/2003 | Falotico |
| 2004/0073296 A1 | 4/2004 | Epstein et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |

FOREIGN PATENT DOCUMENTS

| | | |
|---|---|---|
| EP | 0 294 905 | 12/1988 |
| EP | 0 335 341 | 10/1989 |
| EP | 0 353 341 | 2/1990 |
| EP | 0 375 520 | 6/1990 |
| EP | 0 470 246 | 2/1992 |
| EP | 0 470 569 | 2/1992 |
| EP | 0 551 182 | 7/1993 |
| EP | 0 556 245 | 10/1993 |
| EP | 0 567 816 | 11/1993 |
| EP | 0 568 310 | 11/1993 |
| EP | 0 604 022 | 6/1994 |
| EP | 0 623 354 | 11/1994 |
| EP | 0 627 226 | 12/1994 |
| EP | 0 679 373 | 11/1995 |
| EP | 0 716 836 | 6/1996 |
| EP | 0 734 698 | 10/1996 |
| EP | 0 747 069 | 12/1996 |
| EP | 0 752 885 | 1/1997 |
| EP | 0 706 376 | 6/1997 |
| EP | 0 797 963 | 10/1997 |
| EP | 0 832 655 | 4/1998 |
| EP | 0 850 651 | 7/1998 |
| EP | 0 897 700 | 2/1999 |
| EP | 0 566 245 | 10/1999 |
| EP | 0 950 386 | 10/1999 |
| EP | 1 118 325 | 7/2001 |
| EP | 1 132 058 | 9/2001 |
| EP | 1 172 074 | 1/2002 |
| EP | 1 181 943 | 2/2002 |
| EP | 1 223 305 | 7/2002 |
| EP | 1 236 478 | 9/2002 |
| EP | 0 711 158 | 3/2003 |
| EP | 1 222 941 | 5/2006 |
| EP | 1277449 B1 | 6/2006 |
| FR | 2 764 794 | 12/1998 |
| GB | 20200220 | 4/2002 |
| WO | WO 90/01969 | 3/1990 |
| WO | WO 90/13332 | 11/1990 |
| WO | WO 91/10424 | 7/1991 |
| WO | WO 91/11193 | 8/1991 |
| WO | WO 91/12779 | 9/1991 |
| WO | WO 92/00747 | 1/1992 |
| WO | WO 92/12717 | 8/1992 |
| WO | WO 92/15286 | 9/1992 |
| WO | WO 93/06792 | 4/1993 |
| WO | WO 93/11120 | 6/1993 |
| WO | WO 94/07529 | 4/1994 |
| WO | WO 94/21308 | 9/1994 |
| WO | WO 94/24961 | 11/1994 |
| WO | WO 94/24962 | 11/1994 |
| WO | WO 95/03036 | 2/1995 |
| WO | WO 95/03795 | 2/1995 |
| WO | WO 95/03796 | 2/1995 |
| WO | WO 95/24908 | 9/1995 |
| WO | WO 96/03092 | 2/1996 |
| WO | WO 95/25176 | 8/1996 |
| WO | WO 96/29028 | 9/1996 |
| WO | WO 96/32907 | 10/1996 |

| | | |
|---|---|---|
| WO | WO 97/04721 | 2/1997 |
| WO | WO 97/10011 | 3/1997 |
| WO | WO 98/08566 | 3/1998 |
| WO | WO 98/18407 | 5/1998 |
| WO | WO 98/19628 | 5/1998 |
| WO | WO 98/23228 | 6/1998 |
| WO | WO 98/23244 | 6/1998 |
| WO | WO 9823228 A1 * | 6/1998 |
| WO | WO 98/36784 | 8/1998 |
| WO | WO 98/36784 A1 | 8/1998 |
| WO | WO 98/58600 | 12/1998 |
| WO | WO 99/15108 | 4/1999 |
| WO | WO 99/16477 | 4/1999 |
| WO | WO 99/44536 | 9/1999 |
| WO | WO 99/49928 | 10/1999 |
| WO | WO 99/55395 | 11/1999 |
| WO | WO 00/10613 | 3/2000 |
| WO | WO 00/10622 | 3/2000 |
| WO | WO 00/45744 | 8/2000 |
| WO | WO 00/69368 | 11/2000 |
| WO | WO 00/71054 | 11/2000 |
| WO | WO 01/17577 | 3/2001 |
| WO | WO 01/45763 | 6/2001 |
| WO | WO 01/45862 | 6/2001 |
| WO | WO 01/49338 | 7/2001 |
| WO | WO 01/52915 | 7/2001 |
| WO | WO 01/87376 | 11/2001 |
| WO | WO 02/17880 | 3/2002 |
| WO | WO 02/26162 | 4/2002 |
| WO | WO 02/26281 | 4/2002 |
| WO | WO 02/060506 A1 | 8/2002 |
| WO | WO 02/087586 | 11/2002 |
| WO | WO 03/007842 A2 | 1/2003 |
| WO | WO 03/047463 A1 | 6/2003 |
| WO | WO 2004/043511 | 5/2004 |

OTHER PUBLICATIONS

European Office Action dated Jun. 11, 2010 in Application No. 09009102.6.

Grayson, A.C. Richards et al., "Multi-pulse Drug Delivery From a Resorbable Polymeric Microchip Device", Nature Materials, vol. 2, Nov. 2003, pp. 767-770.

Hakan, E. et al., The Jostent Coronary Stent Range, Ch. 19.

Hiatt, B.L. et al., "The Drug-Eluting Stent: Is it the Holy Grail?" Reviews in Cardiovascular medicine, 2001, vol. 2, No. 4, pp. 190-196.

West, J.L., "Drug-Delivery—Pulsed Polymers", nature Materials, vol. 2, Nov. 2003, pp. 709-710.

Serruys, P. et al., "Heparin-coated Palmaz-Schatz Stents in Human Coronary Arteries" Circulation, 93, 1996, pp. 412-422.

Kornowski, R. et al., "Slow-Release Taxol coated GR11 Stents Reduce Neointima Formation in a Porcine Coronary in Stent Restenosis Model" Abstract from the American Hear Associatiion's 70$^{th}$ Scientific Sessions, Nov. 9-12, 1997.

* cited by examiner

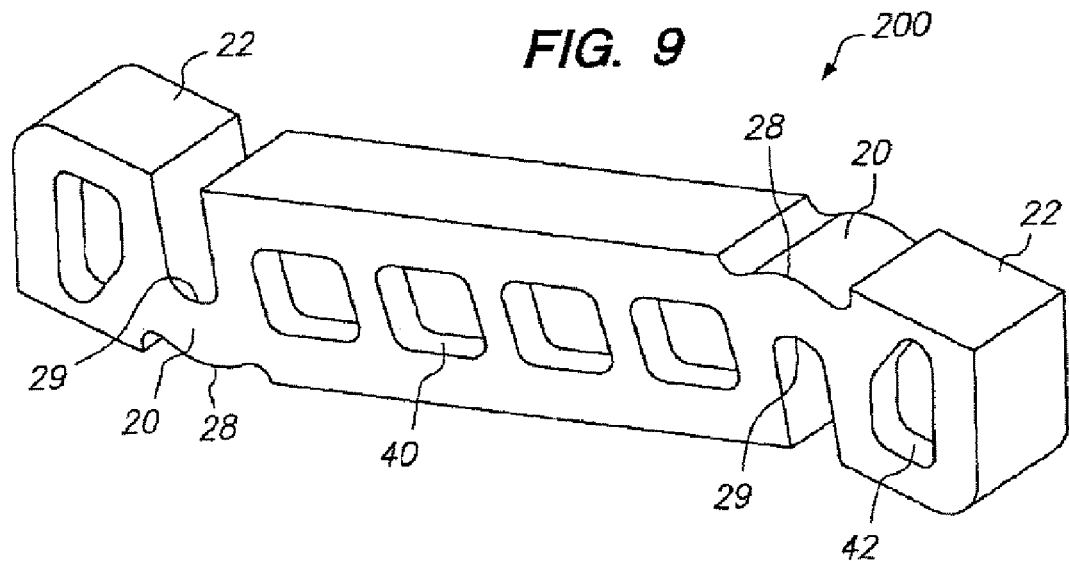
FIG. 9
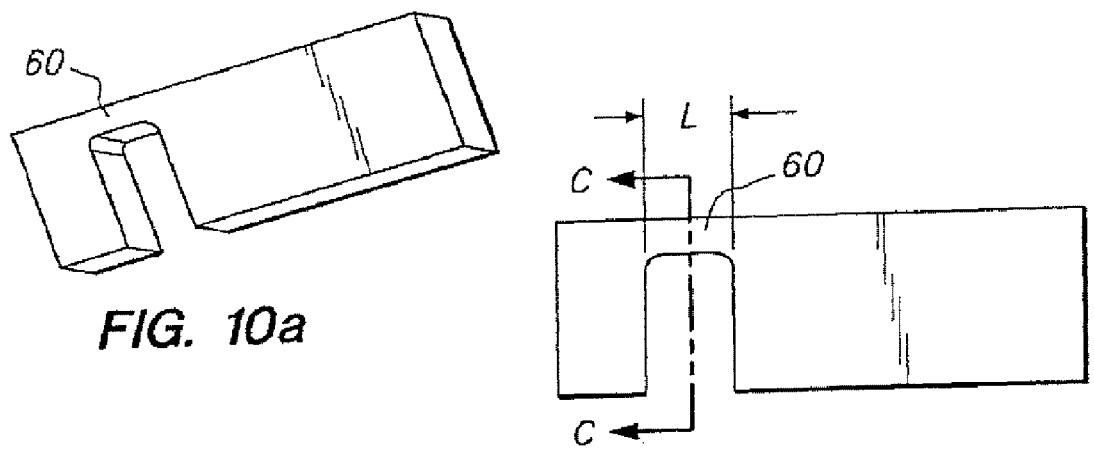
FIG. 10a
FIG. 10b
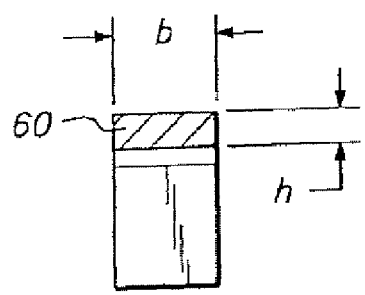
FIG. 10c
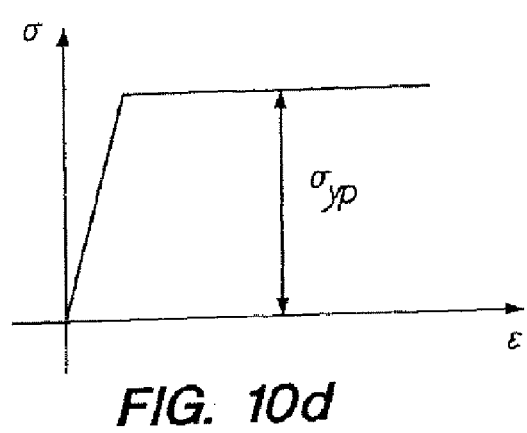
FIG. 10d

EXPANDABLE MEDICAL DEVICE FOR DELIVERY OF BENEFICIAL AGENT

CROSS-REFERENCE TO RELATED APPLICATIONS

This application claims the benefit of priority and is a continuation of U.S. patent application Ser. No. 11/368,957, filed Mar. 6, 2006, which is a continuation of U.S. patent application Ser. No. 10/456,292, filed Jun. 5, 2003, now U.S. Pat. No. 7,179,288, which is a continuation of U.S. patent application Ser. No. 09/688,092, filed on Oct. 16, 2000, now abandoned, which is a continuation-in-part of U.S. application Ser. No. 09/183,555, filed Oct. 29, 1998, now U.S. Pat. No. 6,241,762, which claims the benefit of priority of U.S. Provisional Application No. 60/079,881, filed Mar. 30, 1998, each of which is incorporated herein by reference in its entirety.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency, and that can deliver a beneficial agent to the intervention site.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665, 4,739,762, and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665, 4,739,762, and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. The force required to expand these tubular stents is proportional to the thickness of the wall material in a radial direction. To keep expansion forces within acceptable levels for use within the body (e.g., 5-10 atm), these designs must use very thin-walled materials (e.g., stainless steel tubing with 0.0025 inch thick walls). However, materials this thin are not visible on conventional fluoroscopic and x-ray equipment and it is therefore difficult to place the stents accurately or to find and retrieve stents that subsequently become dislodged and lost in the circulatory system.

Further, many of these thin-walled tubular stent designs employ networks of long, slender struts whose width in a circumferential direction is two or more times greater than thickness in a radial direction. When expanded, these struts are frequently unstable, that is, they display a tendency to buckle, with individual struts twisting out of plane. Excessive protrusion of these twisted struts into the bloodstream has been observed to increase turbulence, and thus encourage thrombosis. Additional procedures have often been required to attempt to correct this problem of buckled struts. For example, after initial stent implantation is determined to have caused buckling of struts, a second, high-pressure balloon (e.g., 12 to 18 atm) would be used to attempt to drive the twisted struts further into the lumen wall. These secondary procedures can be dangerous to the patient due to the risk of collateral damage to the lumen wall.

Many of the known stents display a large elastic recovery, known in the field as "recoil," after expansion inside a lumen. Large recoil necessitates over-expansion of the stent during implantation to achieve the desired final diameter. Over-expansion is potentially destructive to the lumen tissue. Known stents of the type described above experience recoil of up to about 6 to 12% from maximum expansion.

Large recoil also makes it very difficult to securely crimp most known stents onto delivery catheter balloons. As a result, slippage of stents on balloons during interlumenal transportation, final positioning, and implantation has been an ongoing problem. Many ancillary stent securing devices and techniques have been advanced to attempt to compensate for this basic design problem. Some of the stent securing devices include collars and sleeves used to secure the stent onto the balloon.

Another problem with known stem designs is non-uniformity in the geometry of the expanded stent. Non-uniform expansion can lead to non-uniform coverage of the lumen wall creating gaps in coverage and inadequate lumen support. Further, over expansion in some regions or cells of the stent can lead to excessive material strain and even failure of stent features. This problem is potentially worse in low expansion force stents having smaller feature widths and thicknesses in which manufacturing variations become proportionately more significant. In addition, a typical delivery catheter for use in expanding a stent includes a balloon folded into a compact shape for catheter insertion. The balloon is expanded by fluid pressure to unfold the balloon and deploy the stent. This process of unfolding the balloon causes uneven stresses to be applied to the stent during expansion of the balloon due to the folds causing the problem non-uniform stent expansion.

U.S. Pat. No. 5,545,210 discloses a thin-walled tubular stent geometrically similar to those discussed above, but constructed of a nickel-titanium shape memory alloy ("Nitinol"). This design permits the use of cylinders with thicker walls by making use of the lower yield stress and lower elastic modulus of martensitic phase Nitinol alloys. The expansion force required to expand a Nitinol stent is less than that of comparable thickness stainless steel stents of a conventional design. However, the "recoil" problem after expansion is significantly greater with Nitinol than with other materials. For example, recoil of a typical design Nitinol stent is about 9%. Nitinol is also more expensive, and more difficult to fabricate and machine than other stent materials, such as stainless steel.

All of the above stents share a critical design property in each design, the features that undergo permanent deformation during stent expansion are prismatic, i.e., the cross sections of these features remain constant or change very gradually along their entire active length. To a first approximation, such features deform under transverse stress as simple beams with fixed or guided ends; essentially, the features act as a leaf springs. These leaf spring like structures are ideally suited to providing large amounts of elastic deformation before permanent deformation commences. This is exactly the opposite of ideal steal behavior. Further, the force required to deflect prismatic stent struts in the circumferential direction during stent expansion is proportional to the square of the width of the strut in the circumferential direction. Expansion forces thus increase rapidly with strut width in the above stent designs. Typical expansion pressures required to expand known stents are between about 5 and 10 atmospheres. These forces can cause substantial damage to tissue if misapplied.

In addition to the above-mentioned risks to a patient, restenosis is a major complication which can arise following the implantation of stents, using stent devices such as those described above, and other vascular interventions such as angioplasty. Simply defined, restenosis is a wound healing process that reduces the vessel lumen diameter by scar tissue formation and which may ultimately result in reocclusion of the lumen. Despite the introduction of improved surgical techniques, devices and pharmaceutical agents, the overall restenosis rate is still reported in the range of 25% to 50% within six to twelve months after an angioplasty procedure. To correct this problem, additional revascularization procedures are frequently required, thereby increasing trauma and risk to the patient.

Several techniques under development to address the problem of restenosis are irradiation of the injury site and the use of stents to deliver a variety of beneficial or pharmaceutical agents to the traumatized vessel lumen. In the latter case, a stent is frequently surface-coated with a beneficial agent (often a drug-impregnated polymer) and implanted at the angioplasty site. Alternatively, an external drug-impregnated polymer sheath is mounted over the stent and co-deployed in the vessel. In either case, it has proven difficult to deliver a sufficient amount of beneficial agent to the trauma site so as to satisfactorily prevent the growth of scar tissue and thereby reduce the likelihood of restenosis. Even with relatively thick coatings of the beneficial agent or sheaths of increased thickness surrounding the stents, restenosis has been found to occur. Furthermore, increasing the effective stent thickness (e.g., by providing increased coatings of the beneficial agent) is undesirable for a number of reasons, including increased trauma to the vessel lumen during implantation and reduced flow cross-section of the lumen after implantation. Moreover, coating thickness is one of several factors that affect the release kinetics of the beneficial agent, and limitations on thickness thereby limit the range of release rates, durations, and the like that can be achieved.

SUMMARY OF THE INVENTION

In view of the drawbacks of the prior art, it would be advantageous to provide a stent capable of delivering a relatively large volume of a beneficial agent to a traumatized site in a vessel lumen without increasing the effective wall thickness of the stent, and without adversely impacting the mechanical expansion properties of the stent.

It would further be advantageous to have such a stent, which also significantly increases the available depth of the beneficial agent reservoir.

It would be further advantageous to be able to expand such a stent with an expansion force at a low level independent of choice of stent materials, material thickness, or strut dimensions.

It would further be advantageous to have such a tissue-supporting device that permits a choice of material thickness that could be viewed easily on conventional fluoroscopic equipment for any material.

It would also be advantageous to have such a tissue-supporting device that is inherently stable during expansion, thus eliminating buckling and twisting of structural features during stent deployment.

In addition, it would be advantageous to have such a tissue-supporting device with minimal elastic recovery, or "recoil" of the device after expansion.

It would be advantageous to have such a tissue supporting device that can be securely crimped to the delivery catheter without requiring special tools, techniques, or ancillary clamping features.

In accordance with one aspect of the invention, an expandable medical device includes a cylindrical tube, and a network of elongated struts formed in the cylindrical tube, wherein each of the elongated struts are axially displaced from adjacent struts. A plurality of ductile hinges are formed between the elongated struts. The ductile hinges allow the cylindrical tube to be expanded or compressed from a first diameter to a second diameter by deformation of the ductile hinges. Further, at least one of the elongated struts includes at least one opening for loading of a beneficial agent therein. The at least one opening may include a plurality of openings that extend through a thickness of the at least one strut, so as to thereby define a through-opening, or the openings may have a depth less than a thickness of the at least one strut, so as to thereby define a recess. A beneficial agent is loaded within the at least one opening, wherein the beneficial agent includes antiproliferatives, antithrombins, large molecules, microspheres, biodegradable agents, or cells. The at least one opening of the at least one strut forms a protected receptor for loading the beneficial agent therein.

In accordance with a further aspect of the present invention, an expandable medical device includes a plurality of elongated struts, the plurality of elongated struts joined together to form a substantially cylindrical device which is expandable from a cylinder having a first diameter to a cylinder having a second diameter, and the plurality of struts each having a strut width in a circumferential direction. At least one of the plurality of struts includes at least one recess extending at least partially through a thickness of the strut. The at least one recess may extend entirely through the thickness of the strut so as to define a through-opening and the at least one recess may be generally rectangular or polygonal.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 9 is an enlarged side view of a portion of a stent in accordance with yet another preferred embodiment of the present invention;

FIGS. 10a-10c are perspective, side, and cross-sectional views of an idealized ductile hinge for purposes of analysis, and FIG. 10d is a stress/strain curve for the idealized ductile hinge;

DETAILED DESCRIPTION OF THE PREFERRED EMBODIMENTS

Figure 1:
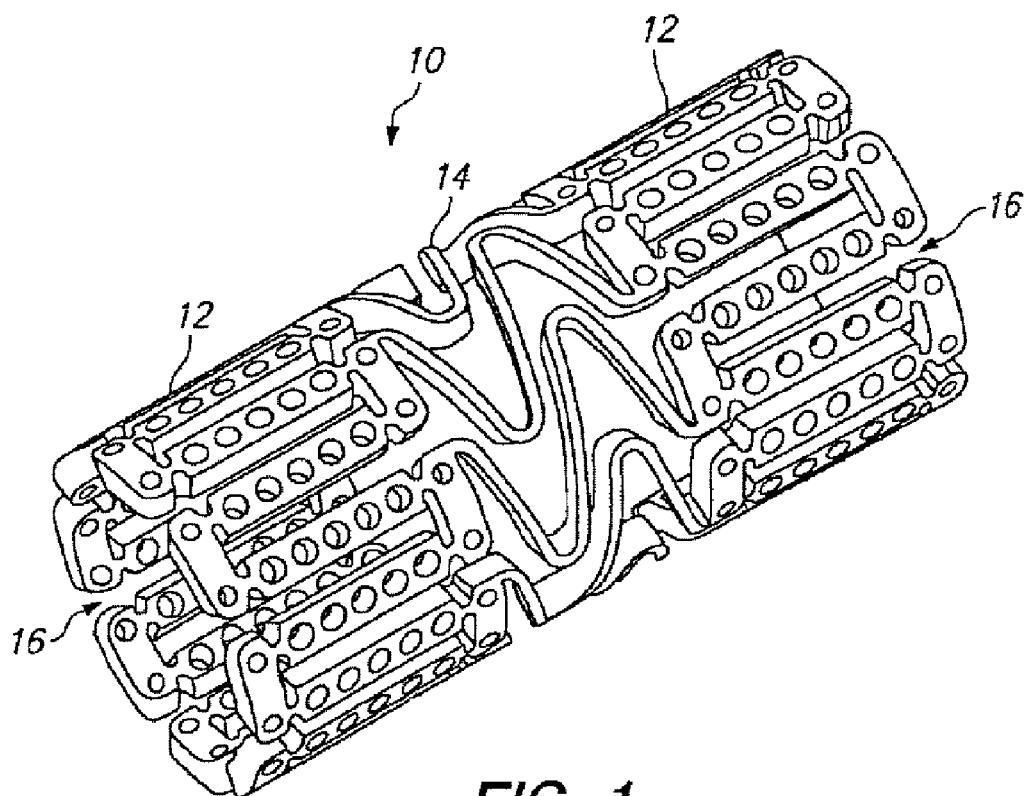
FIG. 1 is a perspective view of a tissue-supporting device in accordance with a first preferred embodiment of the present invention.
Figure 2:
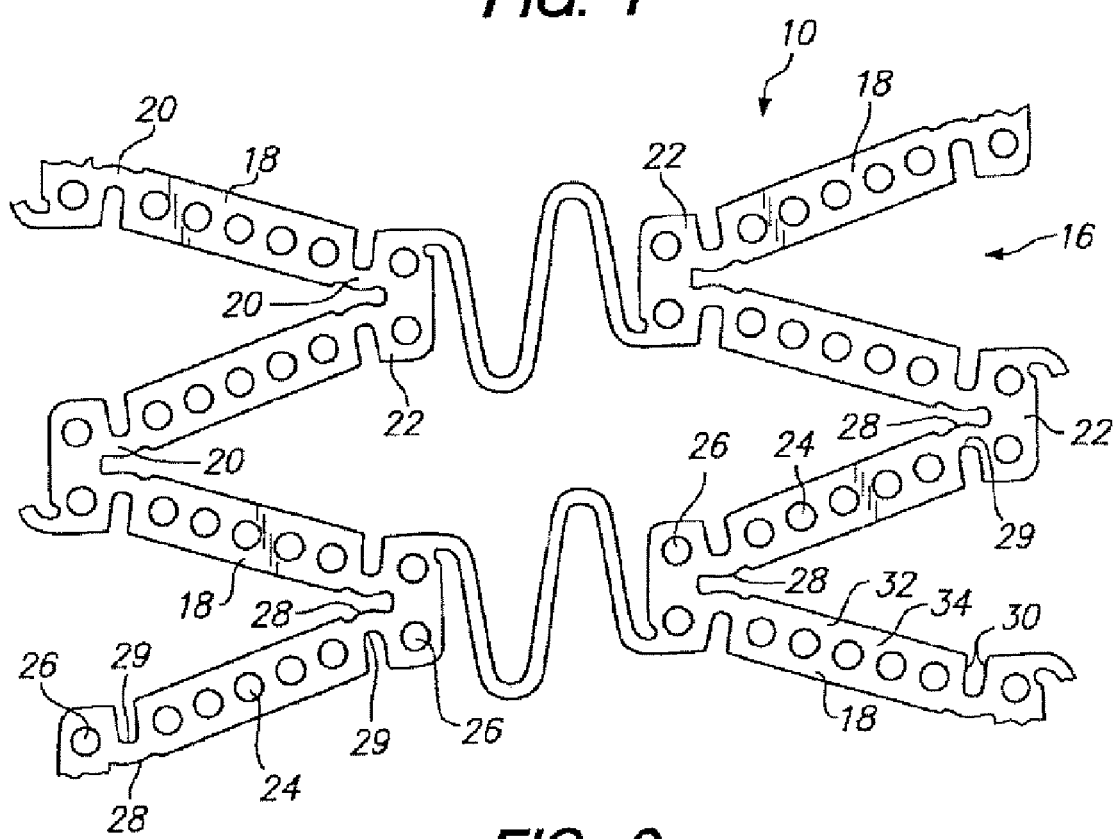
FIG. 2 is an enlarged side view of a portion thereof.

Referring to FIGS. 1 and 2, a tissue supporting device in accordance with a preferred embodiment of the present invention is shown generally by reference numeral 10. The tissue supporting device 10 includes a plurality of cylindrical tubes 12 connected by S-shaped bridging elements 14. The bridging elements 14 allow the tissue supporting device to bend axially when passing through the tortuous path of the vasculature to the deployment site and allow the device to bend when necessary to match the curvature of a lumen to be supported. The S-shaped bridging elements 14 provide improved axial flexibility over prior art devices due to the thickness of the elements in the radial direction which allows the width of the elements to be relatively small without sacrificing radial strength. For example, the width of the bridging elements 14 may be about 0.0015-0.0018 inches (0.0381-0.0457 mm). Each of the cylindrical tubes 12 has a plurality of axial slots 16 extending from an end surface of the cylindrical tube toward an opposite end surface.

Formed between the slots 16 is a network of axial struts 18 and links 22. The cross section (and rectangular moment of inertia) of each of the struts 18 is preferably not constant along the length of the strut. Rather, the strut cross section changes abruptly at both ends of each strut 18 adjoining the links 22. The preferred struts 18 are thus not prismatic. Each individual strut 18 is preferably linked to the rest of the structure through a pair of reduced sections 20, one at each end, which act as stress/strain concentration features. The reduced sections 20 of the struts function as hinges in the cylindrical structure. Since the stress/strain concentration features are designed to operate into the plastic deformation range of generally ductile materials, they are referred to as ductile hinges 20. Such features are also commonly referred to as "Notch Hinges" or "Notch Springs" in ultra-precision mechanism design, where they are used exclusively in the elastic range.

With reference to the drawings and the discussion, the width of any feature is defined as its dimension in the circumferential direction of the cylinder. The length of any feature is defined as its dimension in the axial direction of the cylinder. The thickness of any feature is defined as the wall thickness of the cylinder.

Ductile hinges 20 are preferably asymmetric ductile hinges that produce different strain versus deflection-angle functions in expansion and compression. Each of the ductile hinges 20 is formed between a arc surface 28 and a concave notch surface 29. The ductile hinge 20 according to a preferred embodiment essentially takes the form of a small, prismatic curved beam having a substantially constant cross section. However, a thickness of the curved ductile hinge 20 may vary somewhat as long as the ductile hinge width remains constant along a portion of the hinge length. The width of the curved beam is measure along the radius of curvature of the beam. This small curved beam is oriented such that the smaller concave notch surface 29 is placed in tension in the device crimping direction, while the larger arc surface 28 of the ductile hinges is placed in tension in the device expansion direction. Again, there is no local minimum width of the ductile hinge 20 along the (curved) ductile hinge axis, and no concentration of material strain. During device expansion tensile strain will be distributed along the arc surface 28 of the hinge 20 and maximum expansion will be limited by the angle of the wails of the concave notch 29 which provide a geometric deflection limiting feature. The notches 29 each have two opposed angled walls 30 which function as a stop to limit geometric deflection of the ductile hinge, and thus limit maximum device expansion. As the cylindrical tubes 12 are expanded and bending occurs at the ductile hinges 20, the angled side walls 30 of the notches 29 move toward each other. Once the opposite side walls 30 of a notch come into contact with each other, they resist further expansion of the particular ductile hinge causing further expansion to occur at other sections of the tissue supporting device. This geometric deflection limiting feature is particularly useful where uneven expansion is caused by either variations in the tissue supporting device 10 due to manufacturing tolerances or uneven balloon expansion. Maximum tensile strain can therefore be reliably limited by adjusting the initial length of the arc shaped ductile hinge 20 over which the total elongation is distributed.

The presence of the ductile hinges 20 allows all of the remaining features in the tissue supporting device to be increased in width or the circumferentially oriented component of their respective rectangular moments of inertia—thus greatly increasing the strength and rigidity of these features. The net result is that elastic, and then plastic deformation commence and propagate in the ductile hinges 20 before other structural elements of the device undergo any significant elastic deformation. The force required to expand the tissue supporting device 10 becomes a function of the geometry of the ductile hinges 20, rather than the device structure as a whole, and arbitrarily small expansion forces can be specified by changing hinge geometry for virtually any material wall thickness. In particular, wall thicknesses great enough to be visible on a fluoroscope can be chosen for any material of interest.

In order to get minimum recoil, the ductile hinges 20 should be designed to operate well into the plastic range of the material, and relatively high local strain-curvatures are developed. When these conditions apply, elastic curvature is a very small fraction of plastic or total curvature, and thus when expansion forces are relaxed, the percent change in hinge curvature is very small. When incorporated into a strut network designed to take maximum advantage of this effect, the elastic springback, or "recoil," of the overall stem structure is minimized.

In the preferred embodiment of FIGS. 1 and 2, it is desirable to increase the width of the individual struts 18 between the ductile hinges 20 to the maximum width that is geometrically possible for a given diameter and a given number of struts arrayed around that diameter. The only geometric limitation on strut width is the minimum practical width of the slots 16 which is about 0.002 inches (0.0508 mm) for laser machining. Lateral stiffness of the struts 18 increases as the cube of strut width, so that relatively small increases in strut width significantly increase strut stiffness. The net result of inserting ductile hinges 20 and increasing strut width is that the struts 18 no longer act as flexible leaf springs, but act as essentially rigid beams between the ductile hinges. All radial expansion or compression of the cylindrical tissue supporting device 10 is accommodated by mechanical strain in the hinge features 20, and yield in the hinge commences at very small overall radial expansion or compression.

Yield in ductile hinges at very low gross radial deflections also provides the superior crimping properties displayed by the ductile hinge-based designs. When a tissue supporting device is crimped onto a folded catheter balloon, very little radial compression of the device is possible since the initial fit between balloon and device is already snug. Most stents simply rebound elastically after such compression, resulting in very low clamping forces and the attendant tendency for the stent to slip on the balloon. Ductile hinges, however, sustain significant plastic deformation even at the low deflections occurring during crimping onto the balloon, and therefore a device employing ductile hinges displays much higher clamping forces. The ductile hinge designs according to the present invention may be securely crimped onto a balloon of a delivery catheter by hand or by machine without the need for auxiliary retaining devices commonly used to hold known stents in place.

The ductile hinge 20 illustrated in FIGS. 1 and 2 is exemplary of a preferred structure that will function as a stress/strain concentrator. Many other stress/strain concentrator configurations may also be used as the ductile hinges in the present invention, as shown and described for example in U.S. application Ser. No. 09/183,555, the entire contents of which is hereby incorporated by reference. The geometric details of the stress/strain concentration features or ductile hinges 20 can be varied greatly to tailor the exact mechanical expansion properties to those required in a specific application. The ductile hinges according to the present invention generally include an abrupt change in width of a strut that functions to concentrate stresses and strains in the narrower section of the strut. These ductile hinges also generally include features to limit mechanical deflection of attached struts and features to control material strain during large strut deflections. Although the ductile hinges have been illustrated in FIG. 2 as positioned along the length of the struts 18 and the links 22, they may also be positioned at other locations in other designs without departing from the present invention.

At intervals along the neutral axis of the struts 18, at least one and more preferably a series of through-openings 24 are formed by laser drilling or any other means known to one skilled in the art. Similarly, at least one and preferably a series of through-openings 26 are formed at selected locations in the links 22. Although the use of through-openings 24 and 26 in both the struts 18 and links 22 is preferred, it should be clear to one skilled in the art that through-openings could be formed in only one of the struts and links. In the illustrated embodiment, the through-openings 24, 26 are circular in nature and thereby form cylindrical holes extending through the width of the tissue supporting device 10. It should be apparent to one skilled in the art, however, that through-openings of any geometrical shape or configuration could of course be used without departing from the scope of the present invention.

The behavior of the struts 18 in bending is analogous to the behavior of an I-beam or truss. The outer edge elements 32 of the struts 18 correspond to the I-beam flange and carry the tensile and compressive stresses, whereas the inner elements 34 of the struts 18 correspond to the web of an I-beam which carries the shear and helps to prevent buckling and wrinkling of the faces. Since most of the bending load is carried by the outer edge elements 32 of the struts 18, a concentration of as much material as possible away from the neutral axis results in the most efficient sections for resisting strut flexure. As a result, material can be judiciously removed along the axis of the strut so as to form through-openings 24, 26 without adversely impacting the strength and rigidity of the strut. Since the struts 18 and links 22 thus formed remain essentially rigid during stent expansion, the through-openings 24, 26 are also non-deforming.

The term "agent" as used herein is intended to have its broadest possible interpretation and is used to include any therapeutic agent or drug, as well as any body analyte, such as glucose. The terms "drug" and "therapeutic agent" are used interchangeably to refer to any therapeutically active substance that is delivered to a bodily lumen of a living being to produce a desired, usually beneficial, effect. The present invention is particularly well suited for the delivery of anti-proliferatives (antirestenosis agents) such as paclitaxel and rapamycin for example, and antithrombins such as heparin, for example. Additional uses, however, include therapeutic agents in all the major therapeutic areas including, but not limited to anti-infectives such as antibiotics and antiviral agents; analgesics, including fentanyl, sufentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antpsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antianythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

The through-openings 24, 26 may also be loaded with an agent, most preferably a beneficial agent, for delivery to the lumen in which the tissue support device 10 is deployed.

The term "agent" as used herein is intended to have its broadest possible interpretation and is used to include any therapeutic agent or drug, as well as any body analyte, such as glucose. The terms "drug" and "therapeutic agent" are used interchangeably to refer to any therapeutically active substance that is delivered to a bodily lumen of a living being to produce a desired, usually beneficial, effect. The present invention is particularly well suited for the delivery of anti-proliferatives (antirestenosis agents) such as paclitaxil and rapamycin for example, and antithrombins such as heparin, for example. Additional uses, however, include therapeutic agents in all the major therapeutic areas including, but not limited to: anti-infectives such as antibiotics and antiviral agents; analgesics, including fentanyl, sufentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antianythrnics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers.

The openings form a protected receptor for loading beneficial agents including large molecules, microspheres, beneficial agents within a biodegradable polymer carrier, and cells.

The embodiment of the invention shown in FIGS. 1 and 2 can be further refined by using Finite Element Analysis and other techniques to optimize the deployment of the beneficial agent within the through-openings of the struts and links. Basically, the shape and location of the through-openings 24, 26 can be modified to maximize the volume of the voids while preserving the relatively high strength and rigidity of the struts 18 with respect to the ductile hinges 20.

Figure 3:
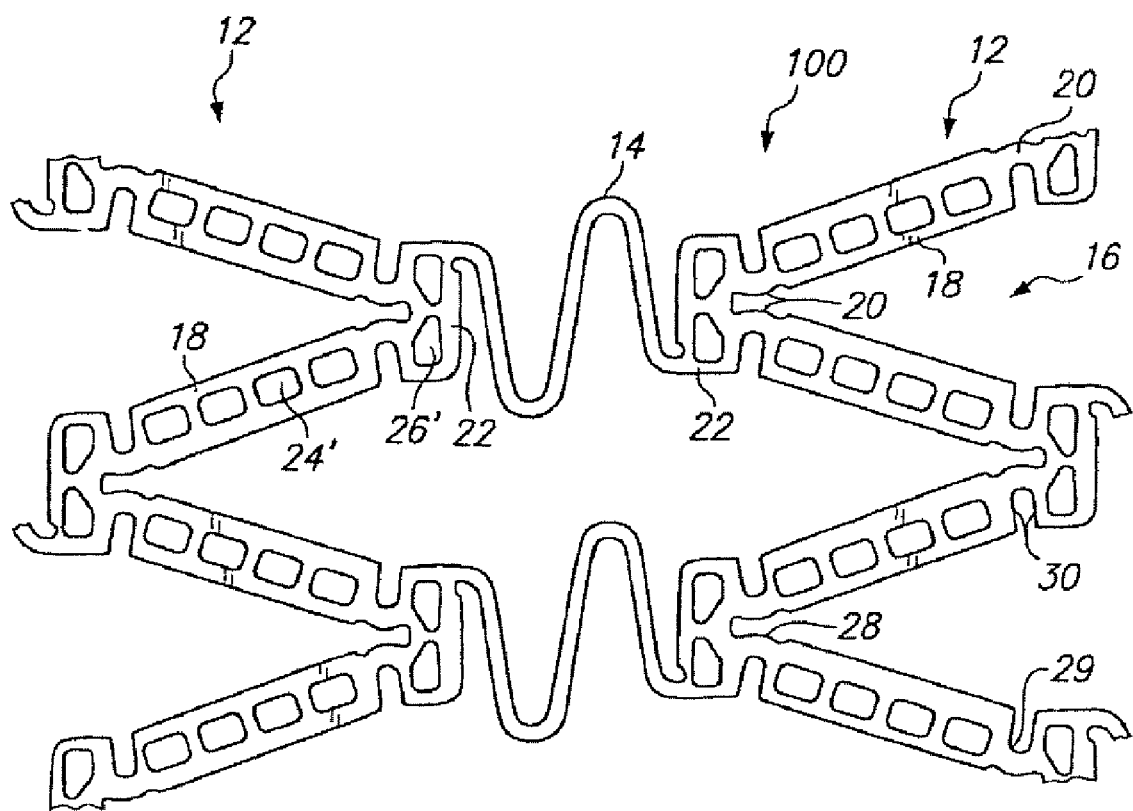
FIG. 3 is an enlarged side view of a tissue-supporting device in accordance with a further preferred embodiment of the present invention.

FIG. 3 illustrates a further preferred embodiment of the present invention, wherein like reference numerals have been used to indicate like components. The tissue supporting device 100 includes a plurality of cylindrical tubes 12 connected by S-shaped bridging elements 14. Each of the cylindrical tubes 12 has a plurality of axial slots 16 extending from an end surface of the cylindrical tube toward an opposite end surface. Formed between the slots 16 is a network of axial struts 18 and links 22. Each individual strut 18 is linked to the rest of the structure through a pair of ductile hinges 20, one at each end, which act as stress/strain concentration features. Each of the ductile hinges 20 is formed between an arc surface 28 and a concave notch surface 29. The notches 29 each have two opposed angled walls 30 which function as a stop to limit geometric deflection of the ductile hinge, and thus limit maximum device expansion.

At intervals along the neutral axis of the struts 18, at least one and more preferably a series of through-openings 24' are formed by laser drilling or any other means known to one skilled in the art. Similarly, at least one and preferably a series of through-openings 26' are formed at selected locations in the links 22. Although the use of through-openings 24' and 26' in both the struts 18 and links 22 is preferred, it should be clear to one skilled in the art that through-openings could be formed in only one of the struts and links. In the illustrated embodiment, the through-openings 24' in the struts 18 are generally rectangular whereas the through-openings 26' in the links 22 are polygonal. It should be apparent to one skilled in the art, however, that through-openings of any geometrical shape or configuration could of course be used, and that the shape of through-openings 24, 24' may be the same or different from the shape of through-openings 26, 26', without departing from the scope of the present invention. As described in detail above, the through-openings 24', 26' may be loaded with an agent, most preferably a beneficial agent, for delivery to the lumen in which the tissue support device 100 is deployed.

The relatively large, protected through-openings 24, 24', 26, 26', as described above, make the expandable medical device of the present invention particularly suitable for delivering agents having more esoteric larger molecules or genetic or cellular agents, such as, for example, protein/enzymes, antibodies, antisense, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large through-openings in the expandable device of the present invention form protected areas or receptors to facilitate the loading of such an agent at the time of use, and to protect the agent from abrasion and extrusion during delivery and implantation.

Figure 4:
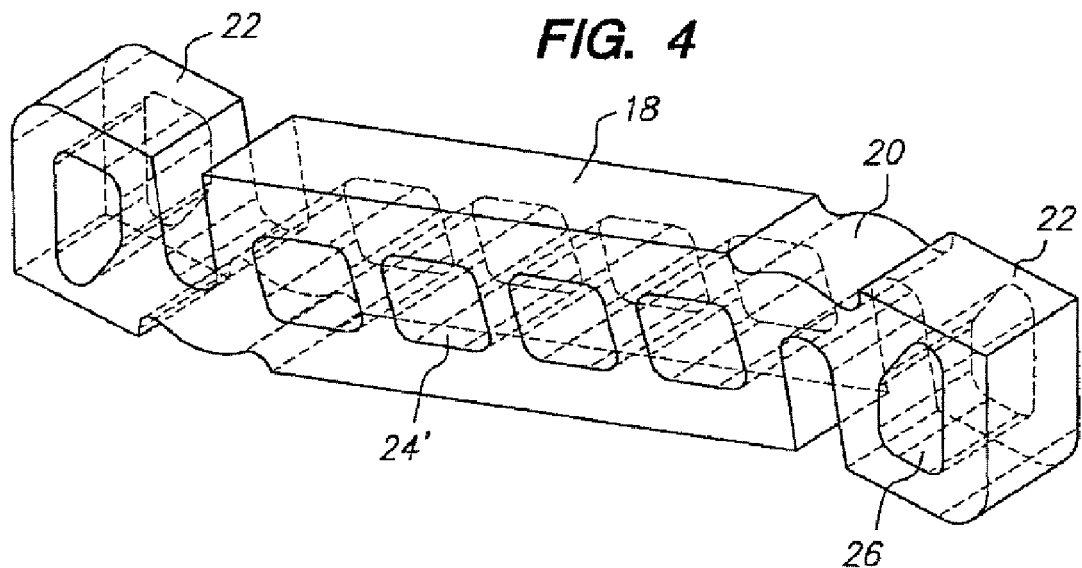
FIG. 4 is an enlarged side view of a portion of the stent shown in the device of FIG. 3.
Figure 5:
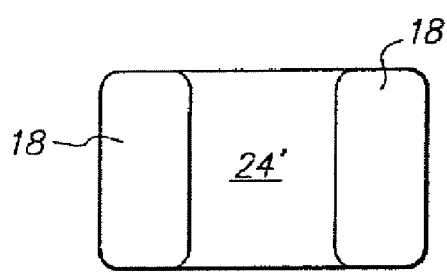
FIG. 5 is an enlarged cross section of an opening thereof.
Figure 6:
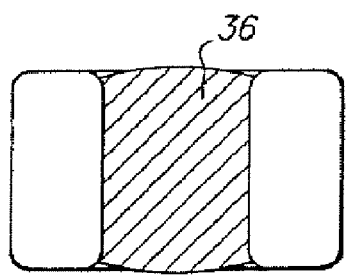
FIG. 6 is an enlarged cross section of an opening thereof illustrating beneficial agent loaded into the opening.
Figure 7:
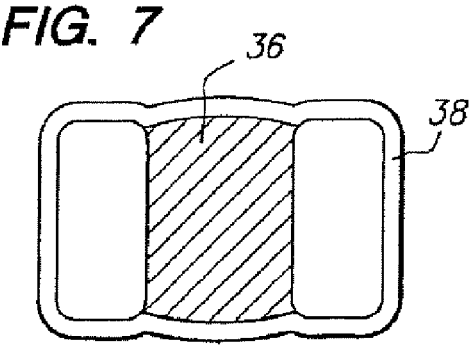
FIG. 7 is an enlarged cross section of an opening thereof illustrating a beneficial agent loaded into the opening and a thin coating of a beneficial agent.
Figure 8:
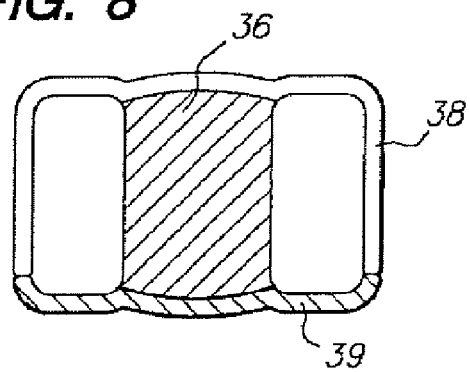
FIG. 8 is an enlarged cross section of an opening thereof illustrating a beneficial agent loaded into the opening and thin coatings of different beneficial agents on different surfaces of the device.

FIG. 4 shows an enlarged view of one of the struts 18 of device 100 disposed between a pair of ductile hinges 20. FIG. 5 illustrates a cross section of one of the openings 24' shown in FIG. 4. FIG. 6 illustrates the same cross section when a beneficial agent 36 has been loaded into the through-openings 24' of the struts 18. Optionally, after loading the through-openings 24' and/or the through-openings 26' with a beneficial agent 36, the entire exterior surface of the stent can be coated with a thin layer of a beneficial agent 38, which may be the same as or different from the beneficial agent 36, as schematically shown in FIG. 7. Still further, another variation of the present invention would coat the outwardly facing surfaces of the stent with a first beneficial agent 38 while coating the inwardly facing surfaces of the stent with a different beneficial agent 39, as illustrated in FIG. 8. The inwardly facing surface of the stent would be defined by at least the surfaces of the stent which, after expansion, forms the inner lumen passage. The outwardly facing surface of the stent would be defined by at least the surface of the stent which, after expansion, is in contact with and directly supports the inner wall of the lumen.

FIG. 9 illustrates yet another preferred embodiment of the present invention, wherein like reference numerals have been used to indicate like components. Unlike the stents 10, 100 described above, tissue supporting device 200 does not include through-openings which extend through the entire width of the stent. Rather, the struts 18 and/or links 22 of stent 200 preferably include at least one and preferably a plurality of recesses 40, 442, formed respectively therein on one or both side surfaces of the stent 200. The recesses 40, 42, also defined as openings, indentations, grooves, and the like, are sufficiently sized so as to promote healing of the endothelial layer and to enable a beneficial agent 36 to be loaded therein. Recesses 40, 42, like through-holes 24, 24', 26, 26', may be formed in struts 18 without compromising the strength and rigidity thereof for the same reasons as noted above. As shown above in FIGS. 7 and 8, a surface coating of one or more beneficial agents may also be provided on stent 200.

The tissue supporting device 10, 100, 200 according to the present invention may be formed of any ductile material, such as steel, gold, silver, tantalum, titanium, Nitinol, other shape memory alloys, other metals, or even some plastics. One preferred method for making the tissue supporting device 10, 100, 200 involves forming a cylindrical tube 12 and then laser cutting the slots 16, notches 29 and through-openings 24, 24', 26, 26' or recesses 40, 42 into the tube. Alternatively, the tissue supporting device may be formed by electromachining, chemical etching followed by rolling and welding, or any other method known to one skilled in the art.

The design and analysis of stress/strain concentration for ductile hinges, and stress/strain concentration features in general, is complex. The stress concentration factor can be calculated for simple ductile hinge geometries, but is generally useful only in the linear elastic range. Stress concentration patterns for a number of other geometries can be determined through photoelastic measurements and other experimental methods. Stent designs based on the use of stress/strain concentration features, or ductile hinges, generally involve more complex hinge geometries and operate in the non-linear elastic and plastic deformation regimes.

The general nature of the relationship among applied forces, material properties, and ductile hinge geometry can be more easily understood through analysis of an idealized hinge 60 as shown in FIGS. 10*a*-10*c*. The hinge 60 is a simple beam of rectangular cross section having a width h, length L and thickness b. The idealized hinge 60 has elastic-ideally-plastic material properties which are characterized by the ideal stress/strain curve of FIG. 10*d*. It can be shown that the "plastic" or "ultimate bending moment" for such a beam is given by the expression:

$$M_p \equiv M_{ult} = \delta_{yp} \frac{bh^2}{4}$$

Where b corresponds to the cylindrical tube wall thickness, h is the circumferential width of the ductile hinge, and $\delta_{yp}$ is the yield stress of the hinge material. Assuming only that expansion pressure is proportional to the plastic moment, it can be seen that the required expansion pressure to expand the tissue supporting device increases linearly with wall thickness b and as the square of ductile hinge width h. It is thus possible to compensate for relatively large changes in wall thickness b with relatively small changes in hinge width h. While the above idealized case is only approximate, empirical measurements of expansion forces for different hinge widths in several different ductile hinge geometries have confirmed the general form of this relationship. Accordingly, for different ductile hinge geometries it is possible to increase the thickness of the tissue supporting device to achieve radiopacity while compensating for the increased thickness with a much smaller decrease in hinge width.

Ideally, the stent wall thickness b should be as thin as possible while still providing good visibility on a fluoroscope. For most stent materials, including stainless steel, this would suggest a thickness of about 0.005-0.007 inches (0.127-0.178 mm) or greater. The inclusion of ductile hinges in a stent design can lower expansion forces/pressures to very low levels for any material thickness of interest. Thus ductile hinges allow the construction of optimal wall thickness tissue supporting devices at expansion force levels significantly lower than current non-visible designs.

The expansion forces required to expand the tissue supporting device 10, 100, 200 according to the present invention from an initial condition illustrated in FIG. 1 to an expanded condition is between 1 and 5 atmospheres, preferably between 2 and 3 atmospheres. The expansion may be performed in a known manner, such as by inflation of a balloon or by a mandrel. The tissue supporting device 10, 100, 200 in the expanded condition has a diameter which is preferably up to three times the diameter of the device in the initial unexpanded condition.

Figure 11:
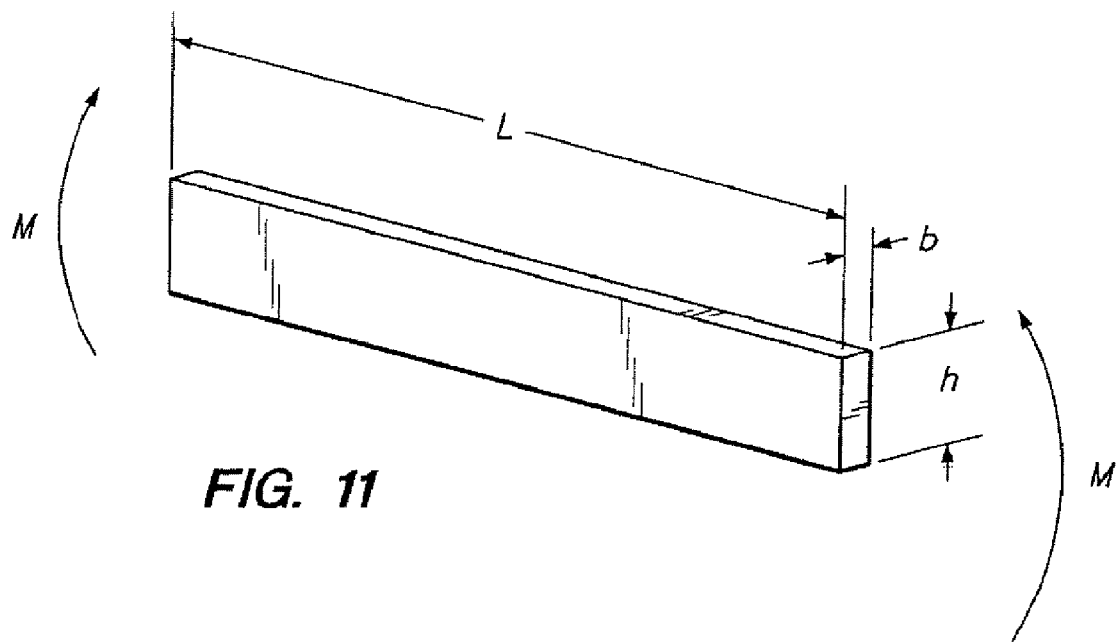
FIG. 11 is a perspective view of a simple beam for purposes of calculation.

Many tissue supporting devices fashioned from cylindrical tubes comprise networks of long, narrow, prismatic beams of essentially rectangular cross section as shown in FIG. 11. These beams which make up the known tissue supporting devices may be straight or curved, depending on the particular design. Known expandable tissue supporting devices have a typical wall thickness b of 0.0025 inches (0.0635 mm), and a typical strut width h of 0.005 to 0.006 inches (0.127-0.1524 mm). The ratio of b:h for most known designs is 1:2 or lower. As b decreases and as the beam length L increases, the beam is increasingly likely to respond to an applied bending moment M by buckling, and many designs of the prior art have displayed this behavior. This can be seen in the following expression for the "critical buckling moment" for the beam of FIG. 6.

$$M_{crit} = \frac{\pi b^3 h \sqrt{EG(1 - 0.63 b/h)}}{6L}$$

Where:

E = Modulus of Elasticity

G = Shear Modulus

By contrast, in a ductile hinge based design according to the present invention, only the hinge itself deforms during expansion. The typical ductile hinge 20 is not a long narrow beam as are the struts in the known stents. Wall thickness of the present invention may be increased to 0.005 inches (0.127 mm) or greater, while hinge width is typically 0.002-0.003 inches (0.0508-0.0762 mm), preferably 0.0025 inches (0.0635 min) or less. Typical hinge length, at 0.002 to 0.005 inches (0.0508-0.0127 mm), is more than an order of magnitude less than typical strut length. Thus, the ratio of b:h in a typical ductile hinge 20 is 2:1 or greater. This is an inherently stable ratio, meaning that the plastic moment for such a ductile hinge beam is much lower than the critical buckling moment $M_{crit}$, and the ductile hinge beam deforms through normal strain-curvature. Ductile hinges 20 are thus not vulnerable to buckling when subjected to bending moments during expansion of the tissue supporting device 10, 100, 200.

To provide optimal recoil and crush-strength properties, it is desirable to design the ductile hinges so that relatively large strains, and thus large curvatures, are imparted to the hinge during expansion of the tissue supporting device. Curvature is defined as the reciprocal of the radius of curvature of the neutral axis of a beam in pure bending. A larger curvature during expansion results in the elastic curvature of the hinge being a small fraction of the total hinge curvature. Thus, the gross elastic recoil of the tissue supporting device is a small fraction of the total change in circumference. It is generally possible to do this because common stent materials, such as 316L-Stainless Steel have very large elongations-to-failure (i.e., they are very ductile).

It is not practical to derive exact expressions for residual curvatures for complex hinge geometries and real materials (i.e., materials with non-idealized stress/strain curves). The general nature of residual curvatures and recoil of a ductile hinge may be understood by examining the moment-curvature relationship for the elastic-ideally-plastic rectangular hinge 60 shown in FIGS. 10*a*-*c*. It may be shown that the relationship between the applied moment and the resulting beam curvature is:

$$M = M_p \left[ 1 - 1/3 \left( \frac{y_0}{h/2} \right)^2 \right] = 3/2 M_{yp} \left[ 1 - 1/3 \left( \frac{\kappa_{yp}}{\kappa} \right)^2 \right]$$

Figure 12:
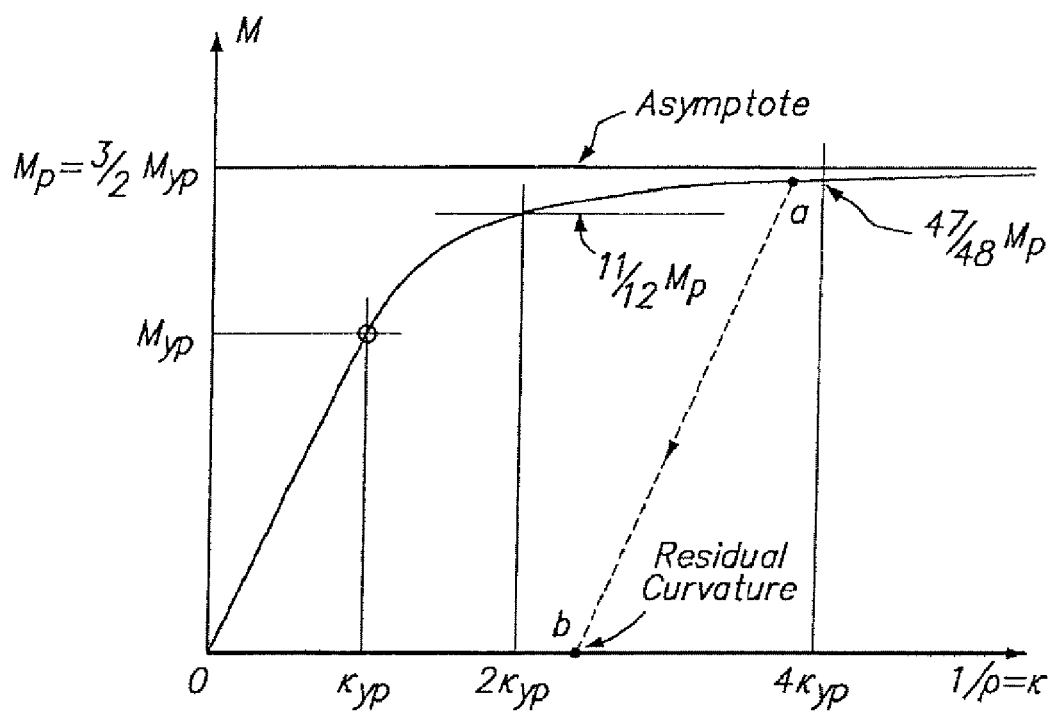
FIG. 12 is a moment verses curvature graph for a rectangular beam.

This function is plotted in FIG. 12. It may be seen in this plot that the applied moment M asymptotically approaches a limiting value $M_P$, called the plastic or ultimate moment. Beyond $^{31}/_{12} M_P$ large plastic deformations occur with little additional increase in applied moment. When the applied moment is removed, the beam rebounds elastically along a line such as a-b. Thus, the elastic portion of the total curvature approaches a limit of 3/2 the curvature at the yield point. These relations may be expressed as follows:

$$M_P = \frac{3}{2}M_{yp} \Rightarrow K_{rebound} = \frac{3}{2}K_{yp}$$

Imparting additional curvature in the plastic zone cannot further increase the elastic curvature, but will decrease the ratio of elastic to plastic curvature. Thus, additional curvature or larger expansion of the tissue supporting device will reduce the percentage recoil of the overall stent structure.

Figure 13:
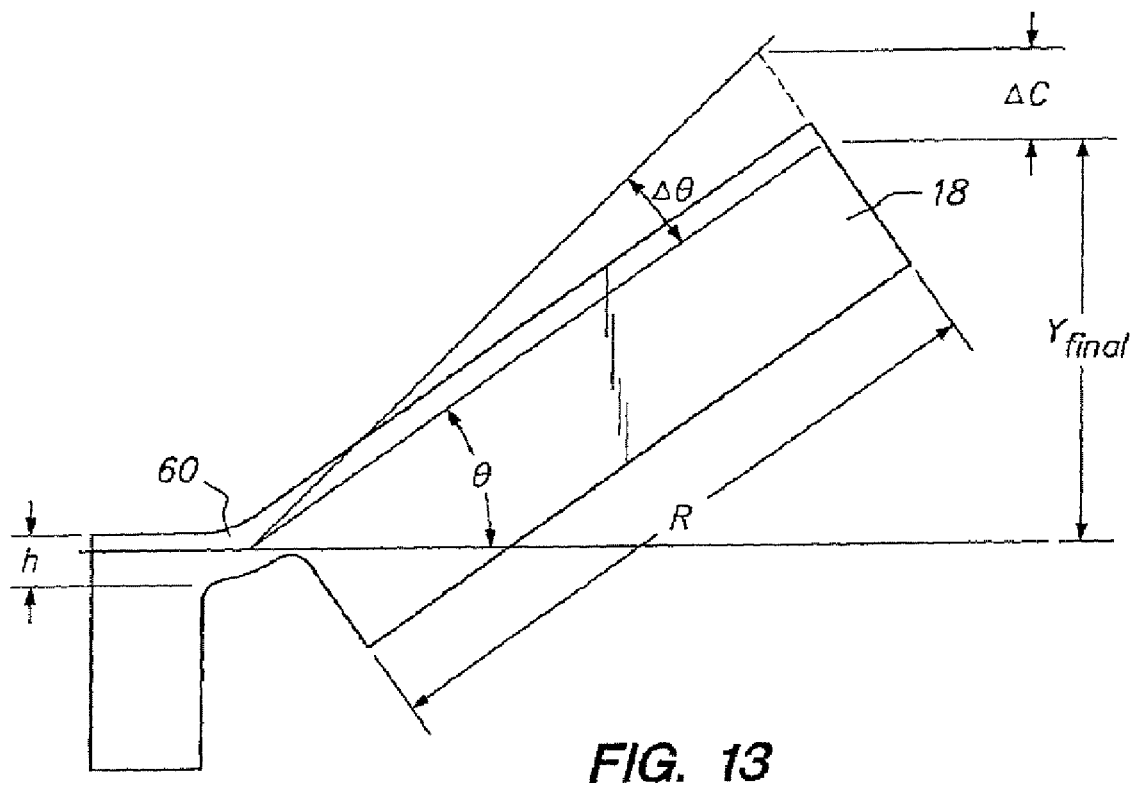
FIG. 13 is an enlarged side view of a bent ductile hinge.

As shown in FIG. 13, when a rigid strut 18 is linked to the ductile hinge 60 described above, the strut 18 forms an angle θ with the horizontal that is a function of hinge curvature. A change in hinge curvature results in a corresponding change in this angle θ. The angular elastic rebound of the hinge is the change in angle Δθ that results from the rebound in elastic curvature described above, and thus angular rebound also approaches a limiting value as plastic deformation proceeds. The following expression gives the limiting value of angular elastic rebound for the idealized hinge of FIG. 13.

$$\theta_{rebound} = 3\varepsilon_{yp}\frac{L}{h}$$

Where strain at the yield point is an independent material property (yield stress divided by elastic modulus); L is the length of the ductile hinge; and h is the width of the hinge. For non-idealized ductile hinges made of real materials, the constant 3 in the above expression is replaced by a slowly rising function of total strain, but the effect of geometry would remain the same. Specifically, the elastic rebound angle of a ductile hinge decreases as the hinge width h increases, and increases as the hinge length L increases, To minimize recoil, therefore, hinge width h should be increased and length L should be decreased.

Ductile hinge width h will generally be determined by expansion force criteria, so it is important to reduce hinge length to a practical minimum in order to minimize elastic rebound. Empirical data on recoil for ductile hinges of different lengths show significantly lower recoil for shorter hinge lengths, in good agreement with the above analysis.

The ductile hinges 20 of the tissue supporting device 10, 100, 200 provide a second important advantage in minimizing device recoil. The embodiment of FIG. 1 shows a network of struts joined together through ductile hinges to form a cylinder. As the device is expanded, curvature is imparted to the hinges 20, and the struts 18 assume an angle θ with respect to their original orientation, as shown in FIG. 13. The total circumferential expansion of the tissue supporting device structure is a function of hinge curvature (strut angle) and strut length. Moreover, the incremental contribution to stent expansion (or recoil) for an individual strut depends on the instantaneous strut angle. Specifically, for an incremental change in strut angle Δθ, the incremental change in circumference ΔC will depend on the strut length R and the cosine of the strut angle θ.

$$\Delta C = R\Delta\theta \cos \theta$$

Since elastic rebound of hinge curvature is nearly constant at any gross curvature, the net contribution to circumferential recoil ΔC is lower at higher strut angles θ. The final device circumference is usually specified as some fixed value, so decreasing overall strut length can increase the final strut angle θ. Total stent recoil can thus be minimized with ductile hinges by using shorter struts and higher hinge curvatures when expanded.

Empirical measurements have shown that tissue supporting device designs based on ductile hinges, such as the embodiment of FIG. 1, display superior resistance to compressive forces once expanded despite their very low expansion force. This asymmetry between compressive and expansion forces may be due to a combination of factors including the geometry of the ductile hinge, the increased wall thickness, and increased work hardening due to higher strain levels.

According to one example of the tissue supporting device of the invention, the device can be expanded by application of an internal pressure of about 2 atmospheres or less, and once expanded to a diameter between 2 and 3 times the initial diameter can withstand a compressive force of about 16 to 20 gm/mm or greater. Examples of typical compression force values for prior art devices are 3.8 to 4.0 gm/mm.

While both recoil and crush strength properties of tissue supporting devices can be improved by use of ductile hinges with large curvatures in the expanded configuration, care must be taken not to exceed an acceptable maximum strain level for the material being used. Generally, $\varepsilon_{max}$ is defined as maximum strain, and it is dependent on ductile hinge width h, ductile hinge length L, and bend angle θ in radians. When strain, hinge width and bend angle are determined through other criteria, an expression may be developed to determine the required lengths for the complicated ductile hinge geometry of the present invention. Typical values for the prismatic portions of the curved ductile hinges 20 range from about 0.002 to about 0.0035 inches (0.051-0.089 mm) in hinge width and about 0.002 to about 0.006 inches (0.051-0.152 mm) in hinge length.

In many designs of the prior art, circumferential expansion was accompanied by a significant contraction of the axial length of the stent which may be up to 15% of the initial device length. Excessive axial contraction can cause a number of problems in device deployment and performance including difficulty in proper placement and tissue damage. Designs based on ductile hinges 20 can minimize the axial contraction, or foreshortening, of a tissue supporting device during expansion, as discussed in greater detail in the a forementioned U.S. application Ser. No. 09/183,555. This ability to control axial contraction based on hinge and strut design provides great design flexibility when using ductile hinges. For example, a stent could be designed with zero axial contraction.

The stent 10, 100, 200 of the present invention illustrates the trade off between crush strength and axial contraction. Referring to FIG. 3, a portion of the tissue supporting device 100 having an array of struts 18 and ductile hinges 20 are shown in the unexpanded state. The struts 18 are positioned initially at an angle $\theta_1$ with respect to a longitudinal axis X of the device, As the device is expanded radially from the unexpanded state illustrated in FIG. 3, the angle $\theta_1$ increases. In this case the device contracts axially from the onset of vertical expansion throughout the expansion. A higher final strut angle $\theta_1$, can significantly increase crush strength and decrease circumferential recoil of the stent structure. However, there is a trade off between increased crush strength and increase in axial contraction.

According to one example of the present invention, the struts 18 are positioned initially at an angle of about 0° to 45° with respect to a longitudinal axis of the device. As the device is expanded radially from the unexpanded state illustrated in FIG. 3, the strut angle increases to about 20° to 80°.

In addition, while ductile hinges 20 are the preferred configuration for the expandable medical device of the present invention, a stent without the defined ductile hinges would also be included within the scope of the present invention.

While the invention has been described in detail with reference to the preferred embodiments thereof, it will be apparent to one skilled in the art that various changes and modifications can be made and equivalents employed, without departing from the present invention.

What is claimed is:

1. An expandable medical device comprising:
    at least two cylindrical tubes connected by S-shaped bridging elements, each of said cylindrical tubes comprising a network of elongated and substantially rigid struts, each elongated and substantially rigid strut having a neutral axis along opposite ends, and inner and outer surfaces defining a thickness;
    a plurality of through-openings in the elongated and substantially rigid struts, said plurality of openings extending through said thickness at intervals along the neutral axis;
    a plurality of ductile hinges interconnecting said elongated and substantially rigid struts, each of said ductile hinges having a reduced section formed at either end of the elongated and substantially rigid strut permitting the expandable medical device to radially expand or compress from a first diameter to a second diameter by first elastically and then plastically deforming, wherein the elongated and substantially rigid struts experience substantially no plastic deformation during expansion or compression from the first diameter to the second diameter;
    at least one beneficial agent contained primarily within the through-openings, said beneficial agent provided in a plurality of layers,
    wherein a width of the ductile hinge is defined as the dimension in the direction perpendicular to a length of the ductile hinge, a thickness of the ductile hinge is defined as the dimension in the radial direction of the device, and the reduced section has a portion of constant width, wherein the inner and outer surfaces of the struts are substantially without beneficial agent thereon, and wherein the ductile hinges are devoid of any openings.

2. The device according to claim 1, wherein the through-openings are formed by laser drilling.

3. The device according to claim 1, wherein the beneficial agent includes at least one antiproliferative.

4. The device according to claim 1, wherein the beneficial agent is paclitaxel.

5. The device according to claim 1, wherein the beneficial agent is a rapamycin.

6. The device according to claim 1, wherein a transition from the elongated strut to the reduced section of the hinge is abrupt.

7. The device according to claim 1, wherein the beneficial agent includes antithrombins.

* * * * *